United States Patent
Ibe et al.

(10) Patent No.: US 9,956,148 B2
(45) Date of Patent: May 1, 2018

(54) OIL-IN-WATER-TYPE EMULSION COSMETIC

(75) Inventors: Ayako Ibe, Yokohama (JP); Yuji Matsushita, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 0 days. days.

(21) Appl. No.: 14/347,328

(22) PCT Filed: Apr. 4, 2012

(86) PCT No.: PCT/JP2012/059166
§ 371 (c)(1),
(2), (4) Date: Mar. 26, 2014

(87) PCT Pub. No.: WO2013/046770
PCT Pub. Date: Apr. 4, 2013

(65) Prior Publication Data
US 2014/0235732 A1    Aug. 21, 2014

(30) Foreign Application Priority Data
Sep. 30, 2011  (JP) ................................ 2011-217339

(51) Int. Cl.
| | | |
|---|---|---|
| A61K 8/31 | (2006.01) | |
| A61K 8/34 | (2006.01) | |
| A61K 8/81 | (2006.01) | |
| A61Q 19/00 | (2006.01) | |
| A61K 8/06 | (2006.01) | |

(52) U.S. Cl.
CPC ............. *A61K 8/31* (2013.01); *A61K 8/062* (2013.01); *A61K 8/342* (2013.01); *A61K 8/8111* (2013.01); *A61Q 19/00* (2013.01)

(58) Field of Classification Search
None
See application file for complete search history.

(56) References Cited

U.S. PATENT DOCUMENTS

| | | | | |
|---|---|---|---|---|
| 4,052,515 A | * | 10/1977 | McDermott | A61K 8/342 514/724 |
| 4,613,447 A | * | 9/1986 | Hara et al. | 15/104.93 |
| 5,002,760 A | * | 3/1991 | Katzev | 424/59 |
| 6,440,431 B1 | * | 8/2002 | Yoshida et al. | 424/401 |
| 7,744,911 B2 | * | 6/2010 | Pechko | A01N 37/18 424/405 |
| 2001/0021429 A1 | * | 9/2001 | Nizuka et al. | 428/36.9 |
| 2013/0079410 A1 | | 3/2013 | Omura et al. | |

FOREIGN PATENT DOCUMENTS

| | | | |
|---|---|---|---|
| EP | 0134483 | * | 3/1985 |
| EP | 2583663 A1 | | 4/2013 |
| JP | 2004-051850 | | 2/2004 |
| JP | 2005-320263 | | 11/2005 |
| JP | 2007-261971 | | 10/2007 |
| JP | 2009-102281 | | 5/2009 |
| JP | 2010-006726 | | 1/2010 |
| JP | 2010-077072 | | 4/2010 |
| JP | 2010-235472 | | 10/2010 |
| JP | 2011-068600 | | 4/2011 |
| WO | 2004012697 A1 | | 2/2004 |

OTHER PUBLICATIONS

Making Cosmetics, Making Emulsions for Cosmetics, http://www.makingcosmetics.com/articles/02-making-emulsions-for-cosmetics.pdf, retrieved online on Sep. 30, 2015.*
Baran et al, Textbook of Cosmetic Dermatology, 1994, https://books.google.com/books?id=rKHSBQAAQBAJ&pg=PA274&lpg=PA274&dq=o/w+emulsion+lotion&source=bl&ots=5fvv36nter&sig=rA-g_S-TjnCmYUVYgPDrh7DPI&hl=en&sa=X&ved=0CHoQ6AEwDWoVChMlp8ORteWSyAIVQ9UeCh3K_Aml#v=onepage&q=o%2Fw%20emulsion%20lotion&f=false.*
Patent Abstracts of Japan, Publication No. 2010-235472, 7 pages.
Patent Abstracts of Japan, Publication No. 2010-006726, 10 pages.
Patent Abstracts of Japan, Publication No. 2007-261971, 10 pages.
Patent Abstracts of Japan, Publication No. 2009-102281, 21 pages.
Patent Abstracts of Japan, Publication No. 2005-320263, 21 pages.
Patent Abstracts of Japan, Publication No. 2004-051850, 7 pages.
Patent Abstracts of Japan, Publication No. 2011-068600, 15 pages.
Patent Abstracts of Japan, Publication No. 2010-077072, 18 pages.
International Search Report, Application No. PCT/JP2012/059166 dated Jun. 19, 2012, 2 pages.
Extended European Search Report dated Mar. 26, 2015 issued in the corresponding European patent application No. 12837089.7.
Dow Corning., "Oil-in-water Foundation: Long Lasting Formulation 00858," Feb. 3, 2006, XP002736886, total 2 pages, Retrieved from the Internet: URL: http://www.dowcorning.com/content/publishedlit/FORMUL_00858.pdf [retrieved on Mar. 5, 2015].; Cited in Extended European Search Report.

* cited by examiner

Primary Examiner — Jennifer A Berrios
(74) Attorney, Agent, or Firm — Rankin, Hill & Clark LLP

(57) ABSTRACT

The present invention provides an oil-in-water emulsion cosmetic that is excellent in the resilient and supple (in other words, firm, tensional, and elastic) feel and also excellent in the softness and moisturizing effect. The oil-in-water emulsion cosmetic of the present invention is characterized by comprising the following components:
(A) 0.1 to 5 mass % of hydrogenated polyisobutene with a number average molecular weight of 2000 to 3000,
(B) 0.1 to less than 1 mass % of higher alcohol,
(C) 1 to 25 mass % of an oil component,
(D) 0.3 to 5 mass % of surfactant,
(E) 0.05 to 5 mass % of water-soluble thickener, and
(F) an aqueous component,
wherein the blending quantity of nonpolar oil is 30% or lower of the total amount of component (C).

11 Claims, No Drawings

OIL-IN-WATER-TYPE EMULSION COSMETIC

RELATED APPLICATIONS

This application claims the priority of Japanese Patent Application No. 2011-217339 filed on Sep. 30, 2011, which is incorporated herein by reference.

FIELD OF THE INVENTION

The present invention relates to an oil-in-water emulsion cosmetic, and in particular, relates to the oil-in-water emulsion cosmetic that is excellent in the resilient and supple (in other words, firm, tensional, and elastic) feel and also excellent in the softness and moisturizing effect.

BACKGROUND OF THE INVENTION

In recent years, it is desired for oil-in-water emulsion cosmetics to impart a resilient and supple feel to the skin (feeling in use wherein the skin does not sag, is not taut, and has moderate elasticity).

In the past, as the material that imparts a resilient and supple feel, polymers and the like have been used. For example, an emulsion cosmetic having a resilient and supple feel, wherein stearyl stearate and a hydrocarbon such as hydrogenated polyisobutene are used in combination, has been known (patent literature 1). However, the resilient and supple feel sometimes becomes weak owing to the moisturizer and oil that are blended to generate a moisturizing effect and other feeling in use.

A skin cosmetic wherein hydrogenated polyisobutene and a specific amount of a higher alcohol are blended has been known (patent literature 2). In addition, an oil-in-water emulsion cosmetic wherein a highly viscous oil such as polybutene is blended has been known (patent literature 3). However, these cosmetics were not satisfactory in the resilient and supple feel.

Patent literature 1: Japanese unexamined patent publication No. 2010-235472
Patent literature 2: Japanese unexamined patent publication No. 2010-6726
Patent literature 3: Japanese unexamined patent publication No. 2007-261971

DISCLOSURE OF THE INVENTION

Problem to be Solved by the Invention

The present invention was made in view of the above-described problems of the conventional art. An object of the invention is to provide an oil-in-water emulsion cosmetic that is excellent in the resilient and supple feel and also excellent in the softness and moisturizing effect.

Means to Solve the Problem

The present inventors have diligently studied to solve the above-described problem. As a result, the present inventors have found that both a resilient/supple feel and softness can be achieved in the oil-in-water emulsion cosmetic that is prepared by blending a specific amount of hydrogenated polyisobutene and a small amount of higher alcohol, thus completing the present invention.

That is, the oil-in-water emulsion cosmetic of the present invention is characterized by comprising the following components:
(A) 0.1 to 5 mass % of hydrogenated polyisobutene with a number average molecular weight of 2000 to 3000,
(B) 0.1 to less than 1 mass % of higher alcohol,
(C) 1 to 25 mass % of an oil component,
(D) 0.3 to 5 mass % of surfactant,
(E) 0.05 to 5 mass % of water-soluble thickener, and
(F) an aqueous component,
wherein the blending quantity of nonpolar oil is 30% or lower of the total amount of component (C).

In the oil-in-water emulsion cosmetic, it is preferable that the viscosity at 25° C. is 50000 mPa·s or lower.

In the oil-in-water emulsion cosmetic, it is preferable that oil-soluble drug is contained in the component (C).

Effect of the Invention

An oil-in-water emulsion cosmetic of the present invention comprises hydrogenated polyisobutene, an oil component comprising a small amount of higher alcohol, surfactant, and an aqueous component comprising water-soluble thickener, and the present invention can provide an oil-in-water emulsion cosmetic that is excellent in the resilient and supple feel and also excellent in the softness and moisturizing effect.

BEST MODE FOR CARRYING OUT THE INVENTION

An oil-in-water emulsion cosmetic of the present invention contains (A) hydrogenated polyisobutene, (B) higher alcohol, (C) an oil component, (D) surfactant, (E) water-soluble thickener, and (F) an aqueous component.

In the following, each component is described in detail.

(A) Hydrogenated Polyisobutene (A) hydrogenated polyisobutene is a hydrocarbon mixture that is obtained by the copolymerization of isobutene and n-butene and the subsequent hydrogenation. As the hydrogenated polyisobutene in the present invention, those commonly used for cosmetics can be used.

It is necessary that the number average molecular weight of the hydrogenated polyisobutene is 2000 to 3000. If the number average molecular weight is too small, the resilient and supple feel may not be satisfactory. If the number average molecular weight is too large, the feeling in use may be affected, for example, the spreadability becomes heavy.

It is necessary that the blending quantity of (A) hydrogenated polyisobutene of the oil-in-water emulsion cosmetic of the present invention is 0.1 to 5 mass % with respect to the total amount of the cosmetic. The blending quantity of component (A) is preferably 0.5 mass % or higher. If it is less than 0.1 mass %, the satisfactory resilient and supple feel cannot be obtained. The blending quantity of component (A) is preferably 3 mass % or lower. If it exceeds 5 mass %, the softness and non-stickiness are poor.

(B) Higher Alcohol

The (B) higher alcohol blended in the oil-in-water emulsion cosmetic of the present invention is an alcohol having 6 or more carbon atoms.

Examples of higher alcohols include behenyl alcohol, stearyl alcohol, cetyl alcohol, myristyl alcohol, and cetostearyl alcohol.

It is necessary that the blending quantity of (B) higher alcohol of the oil-in-water emulsion cosmetic of the present invention is 0.1 to less than 1 mass % with respect to the total amount of the cosmetic. The blending quantity of component (B) is preferably 0.3 mass % or higher. If it is less than 0.1 mass %, the softness and moisturizing effect cannot be obtained. The blending quantity of component (B) is preferably 0.8 mass % or lower. If it is 1 mass % or higher, the resilient and supple feel tend not to be obtained.

(C) Oil Component

The (C) oil component includes other oil components, other than components (A) and (B), normally usable in cosmetics.

Examples of such (C) oil components include liquid oils such as silicon oil, polar oil, and nonpolar oil, solid oil, semisolid oil, and oil-soluble UV absorber.

Examples of silicone oils include liner silicone oils such as dimethylpolysiloxane, methylphenyl polysiloxane, and methylhydrogen polysiloxane, and cyclic silicone oils such as octamethylcyclotetrasiloxane, decamethylcyclopentasiloxane, and dodecamethylcyclohexasiloxane.

Examples of polar oils include ester oils such as glyceryl diisostearate, diisostearyl malate, tripropylene glycol pivalate, glyceryl tri 2-ethylhexanoate, cetyl octanoate, hexyl laurate, isopropyl myristate, octyl palmitate, isocetyl stearate, isopropyl isostearate, octyl isopalmitate, isodecyl isostearate, 2-ethylhexyl succinate, diethyl sebacate, and cetyl ethylhexanoate.

Examples of nonpolar oils include hydrocarbon oils such as liquid paraffin, squalane, squalene, paraffin, and isohexadecane.

Examples of solid oils include solid fats such as cacao butter, coconut oil, horse fat, hydrogenated coconut oil, palm oil, beef fat, mutton suet, and hydrogenated caster oil, hydrocarbons such as paraffin wax (linear hydrocarbon), microcrystalline wax (branched saturated hydrocarbon), ceresin wax, Japan wax, and Fischer-Tropsch wax, waxes such as beeswax, carnauba wax, candelilla wax, rice bran wax (rice wax), spermaceti, jojoba oil, insect wax, montan wax, kapok wax, bayberry wax, shellac wax, sugarcane wax, lanolin fatty acid isopropyl, hexyl laurate, reduced lanolin, hard lanolin, POE lanolin alcohol ether, POE lanolin alcohol acetate, POE cholesterol ether, lanolin fatty acid polyethylene glycol, and POE hydrogenated lanolin alcohol ether, and higher fatty acids such as myristic acid, palmitic acid, stearic acid, and behenic acid.

Examples of semisolid oils include plant oils such as vaseline, lanolin, shea butter, and partial hydrogenated coconut oil, partial hydrogenated jojoba oil, bis-diglyceryl polyacyladipate-2, pentaerythrityl tetra(behenate/benzoate/ethylhexanoate), macadamia seed oil polyglyceryl-6 esters behenate, (phytosteryl/behenyl)dimer dilinoleate, and dipentaerythrityl hexaoxystearate.

Examples of oil-soluble UV absorbers include cinnamic acid-based UV absorbers such as octyl p-methoxycinnamate, isopropyl p-methoxycinnamate, and glyceryl mono-2-ethylhexanoate di-p-methoxycinnamate, benzoic acid-based UV absorbers such as p-aminobenzoic acid, anthranilic acid-based UV absorbers such as methyl anthranilate, salicylic acid-based UV absorbers such as octyl salicylate and phenyl salicylate, 4-tert-butyl-4'-methoxybenzoylmethane, and 2-ethylhexyl 2-cyano-3,3-diphenyl acrylate.

It is preferable that oil-soluble drug is contained as the (C) oil component.

Examples of oil-soluble drugs include oil-soluble vitamins such as vitamin A (retinol), vitamin D, vitamin E, vitamin K, and their derivatives (for example, vitamin A oil and retinol palmitate), oil-soluble derivatives of water-soluble drugs such as vitamin C and arbutin (for example, vitamin C palmitate), oil-soluble plant extract, oil-soluble perfume, surface-hydrophobized material, and cyclosporine.

It is necessary that the blending quantity of (C) oil component of the oil-in-water emulsion cosmetic of the present invention is 1 to 25 mass % with respect to the total amount of the cosmetic. If the blending quantity of component (C) is less than 1 mass %, the moisturizing feel and softness are poor and stickiness is generated. If it exceeds 25 mass %, it becomes oily.

In the present invention, it is necessary that the blending quantity of nonpolar oil is 30% or lower with respect to the total amount of component (C), and it is preferably 20% or lower. If the blending quantity of nonpolar oil in the component (C) exceeds 30% with respect to the total amount of component (C), the resilient and supple feel and non-stickiness may be poor.

On the other hand, as for polar oil, the blending of an oil with high polarity (IOB) is preferable from the standpoint of effectiveness. In particular, the excellent resilient and supple feel can be obtained by blending an oil with the IOB value of 0.3 or higher.

(D) Surfactant

As the (D) surfactant, those normally usable in cosmetics can be used.

It is especially preferable to use a surfactant whose HLB is 5 or higher. If the HLB is less than 5, the lipophilicity is high and it may be difficult to obtain a stable oil-in-water emulsion cosmetic.

The above HLB value can be calculated by Kawakami's equation, which is expressed by $HLB = 7 + 11.7 \cdot \log(MW/MO)$ (here, MW represents the molecular weight of the hydrophilic group, and MO represents the molecular weight of the lipophilic group).

Examples of such surfactants include nonionic surfactant and anionic surfactant.

Examples of nonionic surfactants include polyoxyethylene fatty acid ether, polyoxyethylene fatty acid ester, polyoxyethylene alkyl ether, polyoxyethylene polyoxypropylene alkyl ether, polyoxyethylene alkyl phenyl ether, polyoxyethylene cholesteryl ether, polyoxyethylene phytosterol ether, polyoxyethylene polyoxypropylene phytosterol ether, polyoxyethylene hydrogenated caster oil, polyoxyethylene sorbitan fatty acid ester, polyoxyethylene glyceryl fatty acid ester, polyglycerin fatty acid ester, and sucrose fatty acid ester.

Examples of anionic surfactants include fatty acid soap, N-acyl glutamate, acyl taurine salt, acyl alkyl taurine salt, higher alkyl sulfate ester salt, alkyl ether sulfate ester salt, N-acyl sarcosine acid salt, higher fatty acid amide sulfonate salt, phosphate ester salt, sulfosuccinic acid salt, and alkylbenzene sulfonate.

It is necessary that the blending quantity of (D) surfactant of the oil-in-water emulsion cosmetic of the present invention is 0.3 to 5 mass % with respect to the total amount of the cosmetic. If the blending quantity of component (D) is less than 0.3 mass %, the stability is poor. If it exceeds 5 mass %, the feeling in use is poor.

(E) Water-Soluble Thickener

The (E) water-soluble thickener blended in the present invention includes other water-soluble thickeners normally usable in cosmetics.

Examples of water-soluble thickeners include plant-derived polymers such as gum arabic, tragacanth, galactan, carob gum, guar gum, karaya gum, carrageenan, xanthan gum, pectin, agar, quince seed (quince), and algae colloid (brown algae extract), microorganism-derived polymers such as dextran, succinoglucan, and pullulan, animal-derived polymers such as collagen, casein, albumin, and gelatin, and starch-based polymers such as starch (rice, corn, potato, and wheat), carboxymethyl starch, and methylhydroxypropyl starch.

They also include cellulose polymers such as methyl cellulose, nitrocellulose, ethyl cellulose, methylhydroxypropyl cellulose, hydroxyethyl cellulose, sodium cellulose sulfate, hydroxypropyl cellulose, sodium carboxymethyl cellulose, crystalline cellulose, and cellulose powder, and alginate polymers such as sodium alginate and propylene glycol alginate.

They further include vinyl polymers such as polyvinyl methyl ether and carboxyvinyl polymer, polyoxyethylene polymers, polyoxyethylene/polyoxypropylene copolymers, acrylic polymers such as polyethyl acrylate and polyacrylamide, inorganic water-soluble polymers such as polyethyleneimine, cationic polymer, bentonite, magnesium aluminum silicate, laponite, hectorite, and silicic anhydride, PEG-240/decyltetradeceth-20/hexamethylene diisocyanate copolymer, (dimethylacrylamide/sodium acryloyldimethyltaurine) crosspolymer, (sodium acrylate/sodium acryloyldimethyltaurine) copolymer, (alkyl acrylate/steareth-20 methacrylate) copolymer, and (ammonium acryloyldimethyltaurine/VP) copolymer.

It is necessary that the blending quantity of (E) water-soluble thickener of the oil-in-water emulsion cosmetic of the present invention is 0.05 to 5 mass % with respect to the total amount of the cosmetic. If the blending quantity of component (E) is less than 0.05 mass %, the stability tends to be poor. If the blending quantity exceeds 5 mass %, the feeling in use is poor.

(F) Aqueous Component

The (F) aqueous component includes other aqueous components, other than component (E), normally usable in cosmetics.

Examples of such aqueous components include moisturizer, sequestering agent, antioxidant, water-soluble UV absorber, and water-soluble drug.

Examples of moisturizers include 1,3-butylene glycol, polyethylene glycol, propylene glycol, dipropylene glycol, hexylene glycol, glycerin, diglycerin, xylitol, maltitol, maltose, and D-mannite.

Examples of sequestering agents include sodium edetate, sodium metaphosphate, and phosphoric acid.

Examples of antioxidants include ascorbic acid, dibutylhydroxytoluene, and butylhydroxyanisole.

Examples of water-soluble UV absorbers include benzophenone-based UV absorbers such as 2-hydroxy-4-methoxybenzophenone-5-sulfonic acid and the like, urocanic acid, and phenyl benzimidazole sulfonic acid.

Examples of water-soluble drugs include vitamins such as inositol, pyridoxine hydrochloride, benzyl nicotinate, nicotinamide, dl-alpha-tocopherol nicotinate, magnesium ascorbyl phosphate, ascorbic acid 2-glucoside, L-ascorbic acid dl-alpha-tocopherol phosphoric acid diester potassium salt, pantothenic acid, and biotin, anti-inflammatory agents such as allantoin and azulene, whitening agents such as arbutin, 4-methoxy salicylate or its salt, and tranexamic acid or its derivative, astringent agents such as tannic acid, lysozyme chloride, and marine collagen.

The above-mentioned drugs can be used in a free state, a form of acid or basic salt if one can become salts, or a form of ester if one has a carboxylic acid group.

It is preferable that the blending quantity of (F) aqueous component of the oil-in-water emulsion cosmetic of the present invention is 59 to 96 mass % with respect to the total amount of the cosmetic.

As other components, a powder component such as fine-particle titanium oxide or fine-particle zinc oxide can be blended within the range that the effect of the present invention is not impaired.

In addition, it is preferable that the viscosity of the oil-in-water emulsion cosmetic of the present invention is 50000 mPa·s or lower. In the present invention, the viscosity is a value obtained by the measurement with a viscometer at ordinary temperature (25° C.). If the viscosity is too high, the feeling in use may be poor.

The oil-in-water emulsion cosmetic of the present invention can be widely applied for cosmetics which are commonly applied to the skin, and the specific examples include milky lotion, gel, beauty essence, cream, pre-makeup, foundation, eyeliner, and mascara.

EXAMPLES

The present invention will be further described in the following examples, however, the invention is not limited by these examples. Unless otherwise specified, the blending quantity will be represented as mass % with respect to a system in which each component is blended.

Prior to illustrating the examples, the evaluation methods for the tests used in the present invention will be explained.

Evaluation (1): Stability

The stability was evaluated by comparing the hardness and appearance of a sample stored for 1 month at 25° C. and 40° C. with those of a sample immediately after the preparation.

A*: Under all storage conditions, the decrease of hardness was 10% or less, and no change in appearance was observed.

A: Under all storage conditions, no change in appearance was observed, and the change in the hardness of 10% or higher was observed only for the sample stored at 40° C.

B*: Under all storage conditions, no change in appearance was observed, however, the change in the hardness of 10% or higher was observed.

B: The separation of water or oil was slightly observed in the appearance.

C: Within 1 month, the separation of water or oil was observed in the appearance.

Evaluation (2): Resilient and Supple (in Other Words, Firm, Tensional, and Elastic) Feel 10 professional panelists applied each of the samples to face and evaluated the feeling in use after application.

A*: 9 or more panelists answered that the resilient and supple feel was present.

A: 7 or more and less than 9 panelists answered that the resilient and supple feel was present.

B: 5 or more and less than 7 panelists answered that the resilient and supple feel was present.

C: Less than 5 panelists answered that the resilient and supple feel was present.

Evaluation (3): Non-Stickiness 10 professional panelists applied each of the samples to face and evaluated the feeling in use after application.

A*: 9 or more panelists answered that the stickiness was not present.

A: 7 or more and less than 9 panelists answered that the stickiness was not present.

B: 5 or more and less than 7 panelists answered that the stickiness was not present.

C: Less than 5 panelists answered that the stickiness was not present.

Evaluation (4): Softness 10 professional panelists applied each of the samples to face and evaluated the feeling in use after application.

A*: 9 or more panelists answered that the skin was soft.

A: 7 or more and less than 9 panelists answered that the skin was soft.

B: 5 or more and less than 7 panelists answered that the skin was soft.

C: Less than 5 panelists answered that the skin was soft.

Evaluation (5): Moisturizing Effect 10 professional panelists applied each of the samples to face and evaluated the feeling in use after application.

A*: 9 or more panelists answered that the moisturizing effect was present.
A: 7 or more and less than 9 panelists answered that the moisturizing effect was present.
B: 5 or more and less than 7 panelists answered that the moisturizing effect was present.
C: Less than 5 panelists answered that the moisturizing effect was present.

Thus far, the present inventors have found that the blending of hydrogenated polyisobutene, as the component with high adhesion to the skin and having a resilient and supple feel, is effective in the water-in-oil emulsion cosmetic.

Then, the blending of hydrogenated polyisobutene into the oil-in-water emulsion cosmetic was investigated. Oil-in-water emulsion cosmetics (cream) with the blending compositions shown in the below Table 1 were produced by the ordinary method. Respective samples were evaluated, for the evaluation items (1) to (5), based on the above rating criteria.

The results are shown in Table 1.

TABLE 1

|     |     | Test Example | | |
| --- | --- | --- | --- | --- |
|     |     | 1-1 | 1-2 | 1-3 |
| (A) | Hydrogenated polyisobutene(*1) | — | 3 | 5 |
| (B) | Behenyl alcohol | 2 | 2 | 2 |
|     | Stearyl alcohol | 1.5 | 1.5 | 1.5 |
| (C) | Squalane | 2 | 2 | 2 |
|     | Methyl polysiloxane | 5 | 5 | 5 |
|     | Glyceryl tri(2-ethylhexanoate) | 10 | 10 | 10 |
| (D) | Glyceryl monoisostearate | 1.5 | 1.5 | 1.5 |
|     | POE glycerin monoisostearate | 2 | 2 | 2 |
| (E) | Carboxy vinyl polymer | 0.2 | 0.2 | 0.2 |
| (F) | Water | balance | balance | balance |
|     | Glycerin | 5 | 5 | 5 |
|     | Caustic potash | 0.06 | 0.06 | 0.06 |
|     | Emulsion type | O/W | O/W | O/W |
| Evaluation | (1) Stability | A* | A* | A* |
|     | (2) Resilient and supple feel | C | B | B |
|     | (3) Non-stickiness | A | A* | A* |
|     | (4) Softness | A* | A* | A* |
|     | (5) Moisturizing effect | A | A* | A* |

(*1)Deodorizing polybutene P 200SH (manufactured by NIKKO RICA CORPORATION, number average molecular weight: 3000)

In Test Examples 1-2 and 1-3 wherein hydrogenated polyisobutene was blended to Test Example 1-1, which is an oil-in-water emulsion cosmetic, the resilient and supple feel and the moisturizing effect somewhat improved. However, they turned out to be not completely satisfactory, in particular, in the resilient and supple feel.

The present inventors have blended the hydrogenated polyisobutene and varied the amount of higher alcohol, which was used in combination. Oil-in-water emulsion cosmetics (cream) with the blending compositions shown in the below Table 2 were produced by the ordinary method. Respective samples were evaluated, for the evaluation items (1) to (5), based on the above rating criteria. The results are shown in Table 2.

TABLE 2

|     | Test Example | 2-1 | 2-2 | 2-3 | 2-4 | 2-5 | 2-6 | 1-2 |
| --- | --- | --- | --- | --- | --- | --- | --- | --- |
| (A) | Hydrogenated polyisobutene(*1) | — | 3 | 3 | 3 | 3 | 3 | 3 |
| (B) | Behenyl alcohol | — | — | 0.15 | 0.3 | 0.5 | 1.2 | 2 |
|     | Stearyl alcohol | — | — | 0.1 | 0.2 | 0.3 | 0.8 | 1.5 |
| (C) | Squalane | 2 | 2 | 2 | 2 | 2 | 2 | 2 |
|     | Methyl polysiloxane | 5 | 5 | 5 | 5 | 5 | 5 | 5 |
|     | Glyceryl tri(2-ethylhexanoate) | 10 | 10 | 10 | 10 | 10 | 10 | 10 |
| (D) | Glyceryl monoisostearate | 1.5 | 1.5 | 1.5 | 1.5 | 1.5 | 1.5 | 1.5 |
|     | POE glycerin monoisostearate | 2 | 2 | 2 | 2 | 2 | 2 | 2 |
| (E) | Carboxy vinyl polymer | 0.2 | 0.2 | 0.2 | 0.2 | 0.2 | 0.2 | 0.2 |
| (F) | Water | balance | balance | balance | balance | balance | balance | balance |
|     | Glycerin | 5 | 5 | 5 | 5 | 5 | 5 | 5 |
|     | Caustic potash | 0.06 | 0.06 | 0.06 | 0.06 | 0.06 | 0.06 | 0.06 |
|     | The sum of component (B) | 0 | 0 | 0.25 | 0.5 | 0.8 | 2 | 3.5 |
|     | Emulsion type | O/W | O/W | O/W | O/W | O/W | O/W | O/W |
| Evaluation | (1) Stability | A* | A* | A* | A* | A* | A* | A* |
|     | (2) Resilient and supple feel | C | A* | A* | A* | A | B | B |
|     | (3) Non-stickiness | A | A* | A* | A* | A* | A* | A* |
|     | (4) Softness | B | B | A | A* | A* | A* | A* |
|     | (5) Moisturizing effect | B | A | A* | A* | A* | A* | A* |

As seen from Test Examples 2-3 to 2-5, when a small amount of higher alcohol was blended in the oil-in-water emulsion cosmetic containing the hydrogenated polyisobutene, a cosmetic excellent in the resilient and supple feel could be obtained. In addition, it was clarified that the softness and the moisturizing effect were also excellent.

However, in Test Example 2-2 wherein no higher alcohol was blended, the softness was poor and there was room for improvement in the moisturizing effect.

It was also found that the resilient and supple feel was affected when the blending quantity of higher alcohol was increased.

Accordingly, in the oil-in-water emulsion cosmetic, of the present invention, containing (A) hydrogenated polyisobutene, it is necessary to contain 0.1 to less than 1 mass % of (B) higher alcohol.

Next, the blending quantity of (A) hydrogenated polyisobutene was investigated. Oil-in-water emulsion cosmetics (cream) with the blending compositions shown in the below Table 3 blending varied the amount of hydrogenated polyisobutene were produced by the ordinary method. Respective samples were evaluated, for the evaluation items (1) to (5), based on the above rating criteria. The results are shown in Table 3.

TABLE 3

| Test Example | | 3-1 | 3-2 | 2-4 | 3-3 | 3-4 |
|---|---|---|---|---|---|---|
| (A) | Hydrogenated polyisobutene(*1) | 0.2 | 1 | 3 | 4 | 6 |
| (B) | Behenyl alcohol | 0.3 | 0.3 | 0.3 | 0.3 | 0.3 |
|  | Stearyl alcohol | 0.2 | 0.2 | 0.2 | 0.2 | 0.2 |
| (C) | Squalane | 1 | 2 | 2 | 2 | 4 |
|  | Methyl polysiloxane | 3 | 5 | 5 | 5 | 7 |
|  | Glyceryl tri(2-ethylhexanoate) | 8 | 10 | 10 | 10 | 12 |
| (D) | Glyceryl monoisostearate | 1.5 | 1.5 | 1.5 | 1.5 | 1.5 |
|  | POE glycerin monoisostearate | 2 | 2 | 2 | 2 | 2 |
| (E) | Carboxy vinyl polymer | 0.2 | 0.2 | 0.2 | 0.2 | 0.2 |
| (F) | Water | balance | balance | balance | balance | balance |
|  | Glycerin | 5 | 5 | 5 | 5 | 5 |
|  | Caustic potash | 0.06 | 0.06 | 0.06 | 0.06 | 0.06 |
|  | Emulsion type | O/W | O/W | O/W | O/W | O/W |
| Evaluation | (1) Stability | A* | A* | A* | A* | A* |
|  | (2) Resilient and supple feel | A* | A* | A* | A* | A |
|  | (3) Non-stickiness | A* | A* | A* | A* | A |
|  | (4) Softness | A* | A* | A* | A | B |
|  | (5) Moisturizing effect | A* | A* | A* | A* | A* |

According to Table 3, the resilient and supple feel, the feeling in use and the like were excellent in Test Examples 3-1, 3-2, 2-4, and 3-3, wherein component (A) was suitably blended.

Accordingly, it is necessary that the blending quantity of (A) hydrogenated polyisobutene of the oil-in-water emulsion cosmetic of the present invention is 0.1 to 5 mass %.

Next, the composition of oil was investigated. Oil-in-water emulsion cosmetics (cream) with the blending compositions shown in the below Table 4 were produced by the ordinary method. Respective samples were evaluated, for the evaluation items (1) to (5), based on the above rating criteria. The results are shown in Table 4.

In addition, it was found from the comparison of Test Example 2-4 and Test Example 4-5 that when a part of the high-IOB polar oil was replaced with a low-IOB polar oil, the resilient and supple feel was somewhat suppressed. Accordingly, the blending of a polar oil with high polarity (IOB) is preferable from the standpoint of effectiveness.

Next, the emulsion series was investigated. Water-in-oil emulsion cosmetics (cream) of the below Test Example 5-1 was produced by the ordinary method. Respective samples were evaluated, for the evaluation items (1) to (5), based on the above rating criteria. The results are shown in Table 5.

TABLE 4

| Test Example | | 2-4 | 4-1 | 4-2 | 4-3 | 4-4 | 4-5 |
|---|---|---|---|---|---|---|---|
| (A) | Hydrogenated polyisobutene(*1) | 3 | 3 | 3 | 3 | 3 | 3 |
| (B) | Behenyl alcohol | 0.3 | 0.3 | 0.3 | 0.3 | 0.3 | 0.3 |
|  | Stearyl alcohol | 0.2 | 0.2 | 0.2 | 0.2 | 0.2 | 0.2 |
| (C) | Squalane (Nonpolar oil) | 2 | 3 | 5 | 7 | 9 | 2 |
|  | Methyl polysiloxane | 5 | 5 | 5 | 5 | 5 | 5 |
|  | Glyceryl tri(2-ethylhexanoate) (IOB = 0.36) | 10 | 9 | 7 | 5 | 3 | 5 |
|  | Cetyl ethylhexanoate (IOB = 0.13) | — | — | — | — | — | 5 |
| (D) | Glyceryl monoisostearate | 1.5 | 1.5 | 1.5 | 1.5 | 1.5 | 1.5 |
|  | POE glycerin monoisostearate | 2 | 2 | 2 | 2 | 2 | 2 |
| (E) | Carboxy vinyl polymer | 0.2 | 0.2 | 0.2 | 0.2 | 0.2 | 0.2 |
| (F) | Water | balance | balance | balance | balance | balance | balance |
|  | Glycerin | 5 | 5 | 5 | 5 | 5 | 5 |
|  | Caustic potash | 0.06 | 0.06 | 0.06 | 0.06 | 0.06 | 0.06 |
|  | Nonpolar oil/(C) (%) | 11.8 | 17.6 | 29.4 | 41.2 | 52.9 | 11.8 |
|  | Emulsion type | O/W | O/W | O/W | O/W | O/W | O/W |
| Evaluation | (1) Stability | A* | A* | A* | A* | A* | A* |
|  | (2) Resilient and supple feel | A* | A* | A | B | B | A |
|  | (3) Non-stickiness | A* | A* | A* | A | B | A* |
|  | (4) Softness | A* | A* | A* | A* | A* | A* |
|  | (5) Moisturizing effect | A* | A* | A* | A* | A* | A* |

It was found from Table 4 that when the blending quantity of the nonpolar oil squalane was increased, an oil-in-water emulsion cosmetic satisfactory in the resilient and supple feel and in non-stickiness could not be obtained.

Accordingly, in the oil-in-water emulsion cosmetic of the present invention, it is necessary that the amount of the nonpolar oil is 30% or lower of the total amount of component (C).

TABLE 5

| | | Test Example | |
|---|---|---|---|
| | | 2-4 | 5-1 |
| (A) | Hydrogenated polyisobutene(*1) | 3 | 3 |
| (B) | Behenyl alcohol | 0.3 | — |
|  | Stearyl alcohol | 0.2 | — |

TABLE 5-continued

|   |   | Test Example | |
|---|---|---|---|
|   |   | 2-4 | 5-1 |
| (C) | Squalane | 2 | 2 |
|   | Methyl polysiloxane | 5 | 5 |
|   | Glyceryl tri(2-ethylhexanoate) | 10 | 10 |
| (D) | Glyceryl monoisostearate | 1.5 | — |
|   | POE glycerin monoisostearate | 2 | — |
|   | Dimethyl stearyl ammonium modified hectorite | — | 1.7 |
|   | Polyoxyethylene/methyl polysiloxane copolymer | — | 0.5 |
| (E) | Carboxy vinyl polymer | 0.2 | — |
| (F) | Water | balance | balance |
|   | Glycerin | 5 | 5 |
|   | Caustic potash | 0.06 | — |
|   | Sodium chloride | — | 0.5 |
|   | Emulsion type | O/W | W/O |
| Evaluation | (1) Stability | A* | A |
|   | (2) Resilient and supple feel | A* | B |
|   | (3) Non-stickiness | A* | A |
|   | (4) Softness | A* | B |
|   | (5) Moisturizing effect | A* | A* |

As seen from Table 5, in Test Example 5-1 wherein the emulsion cosmetic was of water-in-oil type, the resilient and supple feel and the softness were poor.

Accordingly, it is necessary that the emulsion cosmetic with the composition of the present invention is of the oil-in-water emulsion series.

Hereinafter, formulation examples of the oil-in-water emulsion cosmetic of the present invention will be illustrated. It is to be understood that the present invention is not limited by these formulation examples.

Formulation Example 1: Milky Lotion

|   |   | (mass %) |
|---|---|---|
| (1) | Water | balance |
| (2) | Glycerin | 8 |
| (3) | Dipropylene glycol | 3 |
| (4) | Xanthane gum | 0.2 |
| (5) | Behenyl alcohol | 0.2 |
| (6) | Stearyl alcohol | 0.16 |
| (7) | Glyceryl monoisostearate | 0.8 |
| (8) | POE glycerin monoisostearate | 1.2 |
| (9) | Squalane | 3 |
| (10) | Methyl phenyl polysiloxane | 6 |
| (11) | Glyceryl diisostearate | 3 |
| (12) | Hydrogenated polyisobutene | 1.5 |

The blending quantity of nonpolar oil/the blending quantity of component (C): 25.0% Viscosity (Vismetron viscometer, VDA type, 12 rpm, rotor No. 3; measurement temperature 25° C.): 4500 mPa·s (Process)

Components (5) to (12) were mixed with heating; thus uniform dispersion was carried out for the oil phase. Components (1) to (4) were mixed with heating to prepare a water phase. The heated oil phase was added to the water phase, and the intended milky lotion was produced by adjusting emulsion particles with a homogenizer and cooling with stirring.

The stability of the obtained milky lotion was good, and it had an excellent use feeling in both resilient/supple feel and skin softness.

Formulation Example 2: Gel

|   |   | (mass %) |
|---|---|---|
| (1) | Water | balance |
| (2) | Glycerin | 5 |
| (3) | Dipropylene glycol | 5 |
| (4) | Sodium polyacrylate/sodium acryloyl dimethyl taurine copolymer | 2.5 |
| (5) | Behenyl alcohol | 0.15 |
| (6) | Stearyl alcohol | 0.07 |
| (7) | Sorbitan monoisostearate | 0.5 |
| (8) | POE glycerin monoisostearate | 0.8 |
| (9) | Squalane | 2 |
| (10) | Methyl phenyl polysiloxane | 3 |
| (11) | Pentaerythritol tetra 2-ethylhexanoate | 4 |
| (12) | Isononyl isononanoate | 2 |
| (13) | Hydrogenated polyisobutene | 2 |

The blending quantity of nonpolar oil/the blending quantity of component (C): 18.2% Viscosity (Vismetron viscometer, VDA type, 12 rpm, rotor No. 3; measurement temperature 25° C.): 34600 mPa·s (Process)

Components (5) to (13) were mixed with heating; thus uniform dispersion was carried out for the oil phase. Components (1) to (4) were mixed with heating to prepare a water phase. The heated oil phase was added to the water phase, and the intended gel was produced by adjusting emulsion particles with a homogenizer and cooling with stirring.

The stability of the obtained gel was good, and it had an excellent use feeling in both resilient/supple feel and skin softness.

Formulation Example 3: Beauty Essence

|   |   | (mass %) |
|---|---|---|
| (1) | Water | balance |
| (2) | Glycerin | 8 |
| (3) | Dipropylene glycol | 3 |
| (4) | Carbomer | 0.2 |
| (5) | Caustic potash | 0.06 |
| (6) | Behenyl alcohol | 0.2 |
| (7) | Stearyl alcohol | 0.16 |
| (8) | Glyceryl monoisostearate | 0.8 |
| (9) | POE glycerin monoisostearate | 1.2 |
| (10) | Squalane | 3 |
| (11) | Methyl polysiloxane | 2 |
| (12) | Cetyl ethylhexanoate | 3 |
| (13) | Diisostearyl malate | 5 |
| (14) | Hydrogenated polyisobutene | 1.5 |
| (15) | Retinol | 0.05 |

The blending quantity of nonpolar oil/the blending quantity of component (C): 23.1% Viscosity (Vismetron viscometer, VDA type, 12 rpm, rotor No. 3; measurement temperature 25° C.): 7900 mPa·s (Process)

Components (6) to (15) were mixed with heating; thus uniform dispersion was carried out for the oil phase. Components (1) to (5) were mixed with heating to prepare a water phase. The heated oil phase was added to the water phase, and the intended beauty essence was produced by adjusting emulsion particles with a homogenizer and cooling with stirring.

The stability of the obtained beauty essence was good, and it had an excellent use feeling in both resilient/supple feel and skin softness.

What is claimed is:

1. An oil-in-water emulsion cosmetic consisting of the following components:
    (A) 0.1 to 5 mass % of hydrogenated polyisobutene with a number average molecular weight of 2000 to 3000 with respect to a total amount of the cosmetic,
    (B) 0.1 to 0.8 mass % of higher alcohol having 16 to 22 carbon atoms with respect to the total amount of the cosmetic,
    (C) 1 to 25 mass % of an oil component including nonpolar oil with respect to the total amount of the cosmetic,
    (D) 0.3 to 5 mass % of surfactant with respect to the total amount of the cosmetic,
    (E) 0.05 to 5 mass % of water-soluble thickener with respect to the total amount of the cosmetic, the water-soluble thickener being one or more selected from a group consisting of carboxyvinyl polymer, xanthan gum, methyl cellulose, dimethylacrylamide/sodium acryloyldimethyltaurine crosspolymer, sodium polyacrylate/sodium acryloyl dimethyl taurine copolymer and ammonium acryloyldimethyltaurine/VP copolymer, and
    (F) an aqueous component,
wherein a blending quantity of the nonpolar oil is more than 0 mass % and 30 mass % or lower of the total amount of component (C).

2. The oil-in-water emulsion cosmetic according to claim 1, wherein the viscosity at 25° C. is 50000 mPa·s or lower.

3. The oil-in-water emulsion cosmetic according to claim 1, wherein an oil-soluble drug is contained in component (C).

4. The oil-in-water emulsion cosmetic according to claim 2, wherein an oil-soluble drug is contained in component (C).

5. An oil-in-water emulsion cosmetic consisting of the following components:
    (A) 0.1 to 5 mass % of hydrogenated polyisobutene with a number average molecular weight of 2000 to 3000 with respect to a total amount of the cosmetic,
    (B) 0.1 to 0.8 mass % of higher alcohol having 16 to 22 carbon atoms with respect to the total amount of the cosmetic,
    (C) 1 to 25 mass % of an oil component including non-polar oil with respect to the total amount of the cosmetic,
    (D) 0.3 to 5 mass % of surfactant with respect to the total amount of the cosmetic,
    (E) 0.05 to 5 mass % of water-soluble thickener with respect to the total amount of the cosmetic, the water-soluble thickener being one or more selected from a group consisting of carboxyvinyl polymer, xanthan gum, methyl cellulose, dimethylacrylamide/sodium acryloyldimethyltaurine crosspolymer, sodium polyacrylate/sodium acryloyl dimethyl taurine copolymer and ammonium acryloyldimethyltaurine/VP copolymer, and
    (F) at least one aqueous component selected from the group consisting of water, a moisturizer, a sequestering agent, an antioxidant, a water-soluble UV absorber, and a water-soluble drug,
wherein a blending quantity of the nonpolar oil is more than 0 mass % and 30 mass % or lower of the total amount of component (C).

6. The oil-in-water emulsion cosmetic according to claim 5, wherein
    the moisturizer is at least one selected from the group consisting of 1,3-butylene glycol, polyethylene glycol, propylene glycol, dipropylene glycol, hexylene glycol, glycerin, diglycerin, xylitol, maltitol, maltose, and D-mannite,
    the sequestering agent is at least one selected from the group consisting of sodium edetate, sodium metaphosphate, and phosphoric acid,
    the antioxidants is at least one selected from the group consisting of ascorbic acid, dibutylhydroxytoluene, and butylhydroxyanisole,
    the water-soluble UV absorber is at least one selected from the group consisting of 2-hydroxy-4-methoxybenzophenone-5-sulfonic acid, urocanic acid, and phenyl benzimidazole sulfonic acid, and
    the water-soluble drugs is at least one selected from the group consisting of inositol, pyridoxine hydrochloride, benzyl nicotinate, nicotinamide, dl-alpha-tocopherol nicotinate, magnesium ascorbyl phosphate, ascorbic acid 2-glucoside, L-ascorbic acid dl-alpha-tocopherol phosphoric acid diester potassium salt, pantothenic acid, biotin, allantoin, azulene, arbutin, 4-methoxy salicylate or its salt, tranexamic acid or its derivative, tannic acid, lysozyme chloride, and marine collagen.

7. An oil-in-water emulsion cosmetic consisting of the following components:
    (A) 0.1 to 5 mass % of hydrogenated polyisobutene with a number average molecular weight of 2000 to 3000 with respect to a total amount of the cosmetic,
    (B) 0.1 to 0.8 mass % of higher alcohol having 16 to 22 carbon atoms with respect to the total amount of the cosmetic,
    (C) 1 to 25 mass % of an oil component including nonpolar oil with respect to the total amount of the cosmetic,
    (D) 0.3 to 5 mass % of surfactant with respect to the total amount of the cosmetic,
    (E) 0.05 to 5 mass % of water-soluble thickener with respect to the total amount of the cosmetic, the water-soluble thickener being one or more selected from a group consisting of carboxyvinyl polymer, xanthan gum, methyl cellulose, (dimethylacrylamide/sodium acryloyldimethyltaurine) crosspolymer, sodium polyacrylate/sodium acryloyl dimethyl taurine copolymer and (ammonium acryloyldimethyltaurine/VP) copolymer,
    (F) water and at least one selected from the group consisting of a moisturizer, a sequestering agent, an antioxidant, a water-soluble UV absorber, and a water-soluble drug, and
    (G) fine-particle titanium oxide or fine-particle zinc oxide,
wherein a blending quantity of nonpolar oil is more than 0 mass % and 30 mass % or lower of the total amount of component (C).

8. The oil-in-water emulsion cosmetic according to claim 7, wherein
    the moisturizer is at least one selected from the group consisting of 1,3-butylene glycol, polyethylene glycol, propylene glycol, dipropylene glycol, hexylene glycol, glycerin, diglycerin, xylitol, maltitol, maltose, and D-mannite,
    the sequestering agent is at least one selected from the group consisting of sodium edetate, sodium metaphosphate, and phosphoric acid,
    the antioxidants is at least one selected from the group consisting of ascorbic acid, dibutylhydroxytoluene, and butylhydroxyanisole, the water-soluble UV absorber is at least one selected from the group consisting of 2-hydroxy-4-methoxybenzophenone-5-sulfonic acid, urocanic acid, and phenyl benzimidazole sulfonic acid, and the water-soluble drugs is at least one selected from the group consisting of inositol, pyridoxine hydrochloride, benzyl nicotinate, nicotinamide, dl-alpha-tocopherol nicotinate, magnesium ascorbyl phosphate, ascorbic acid 2-glucoside, L-ascorbic acid dl-alpha-tocopherol phosphoric acid diester potassium salt, pantothenic acid, biotin, allantoin, azulene, arbutin, 4-methoxy salicylate or its salt, tranexamic acid or its derivative, tannic acid, lysozyme chloride, and marine collagen.

9. The oil-in-water emulsion cosmetic according to claim 1, wherein the blending quantity of the nonpolar oil is 8.3 mass % or higher and 30 mass % or lower of the total amount of component (C).

10. The oil-in-water emulsion cosmetic according to claim 5, wherein the blending quantity of the nonpolar oil is 8.3 mass % or higher and 30 mass % or lower of the total amount of component (C).

11. The oil-in-water emulsion cosmetic according to claim 7, wherein the blending quantity of the nonpolar oil is 8.3 mass % or higher and 30 mass % or lower of the total amount of component (C).

* * * * *